(12) United States Patent
Takano et al.

(10) Patent No.: US 7,679,730 B2
(45) Date of Patent: Mar. 16, 2010

(54) SURFACE INSPECTION APPARATUS AND SURFACE INSPECTION METHOD FOR STRAINED SILICON WAFER

(75) Inventors: Hideaki Takano, Shibata (JP); Miyuki Shimizu, Nishikanbara-gun (JP); Takeshi Senda, Shibata (JP); Koji Izunome, Shibata (JP); Yoshinori Hayashi, Fujisawa (JP); Kazuhiko Hamatani, Yokohama (JP)

(73) Assignees: Shibaura Mechatronics Corporation, Kanagawa (JP); Covalent Materials Corporation, Tokyo (JP)

( * ) Notice: Subject to any disclaimer, the term of this patent is extended or adjusted under 35 U.S.C. 154(b) by 222 days.

(21) Appl. No.: 11/908,554

(22) Filed: Sep. 13, 2007

(65) Prior Publication Data
US 2009/0066933 A1    Mar. 12, 2009

Related U.S. Application Data

(63) Continuation of application No. PCT/JP2006/306182, filed on Mar. 27, 2006.

(30) Foreign Application Priority Data
Mar. 28, 2005   (JP)   ............... 2005-093027

(51) Int. Cl.
*G01B 11/16*   (2006.01)
(52) U.S. Cl. .............. 356/32; 73/760; 73/800
(58) Field of Classification Search .......... 356/32; 73/760, 800
See application file for complete search history.

(56) References Cited

U.S. PATENT DOCUMENTS

| | | | | |
|---|---|---|---|---|
| 5,864,393 | A * | 1/1999 | Maris | 356/28 |
| 7,295,307 | B2 * | 11/2007 | Naka et al. | 356/301 |
| 7,327,444 | B2 * | 2/2008 | Naka et al. | 356/73 |
| 7,460,216 | B2 * | 12/2008 | Lecomte et al. | 356/32 |
| 2007/0146685 | A1 * | 6/2007 | Yoo et al. | 356/32 |

FOREIGN PATENT DOCUMENTS

| | | |
|---|---|---|
| JP | 57178135 | 11/1982 |
| JP | 10242227 | 9/1998 |
| JP | 2002365234 | 12/2002 |
| JP | 2004363510 | 12/2004 |

OTHER PUBLICATIONS

Analysis Handbook for ULSI Production, Edited by Tsuneo Ajioka et al., Realize Corporation, 1994, pp. 392-397.
English translation of the International Preliminary Report on Patentability which issued in the parent International Application No. PCT/JP2007/306182.

* cited by examiner

*Primary Examiner*—Roy Punnoose
(74) *Attorney, Agent, or Firm*—Volpe and Koenig P.C.

(57) ABSTRACT

An image pickup device disposed in a predetermined position relative to a surface of a strained silicon wafer photographs the surface of the strained silicon wafer in a plurality of rotation angle positions on photographing conditions under which bright lines appearing on the surface of the strained silicon wafer can be photographed, in an environment where a light source device illuminates the surface of the strained silicon wafer which is rotating. A composite image in a predetermined angle position is generated from surface images of the strained silicon wafer in a plurality of rotation angle positions obtained by the image pickup device.

8 Claims, 14 Drawing Sheets

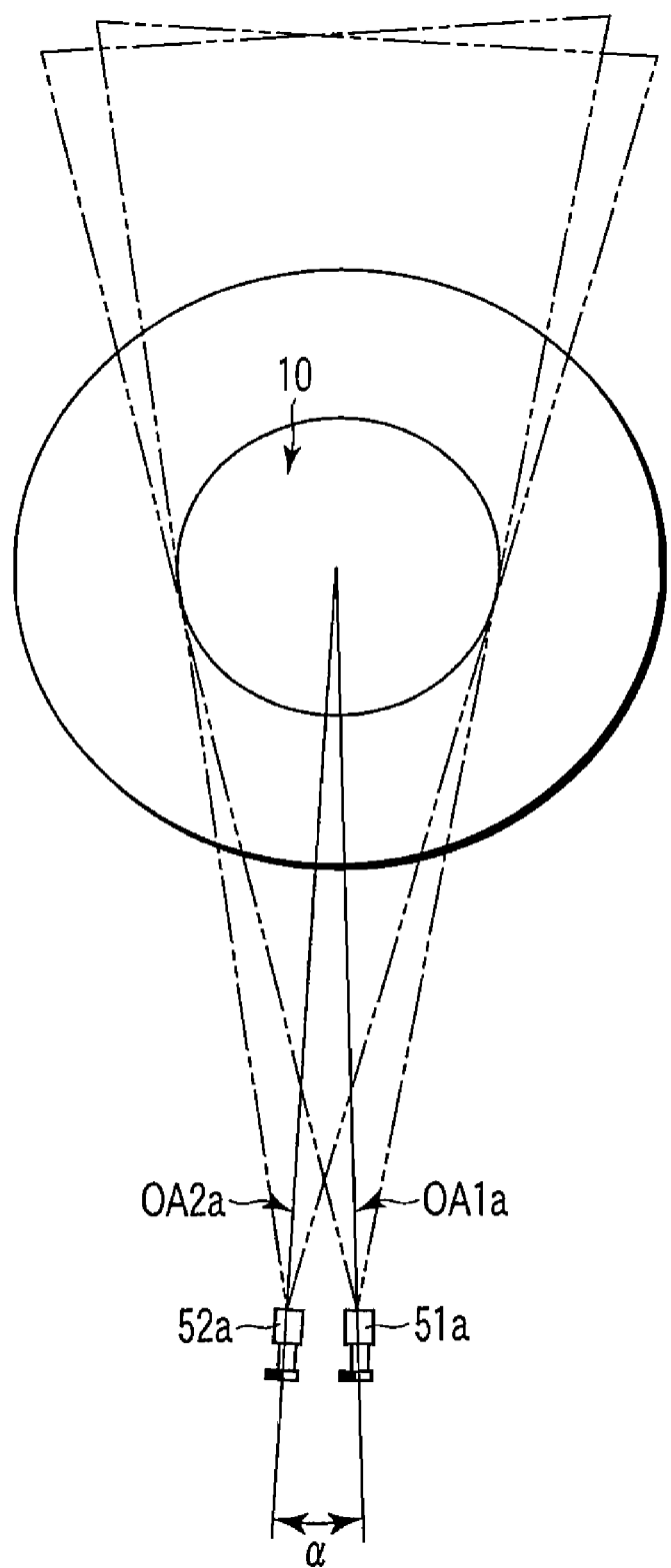
F I G. 2

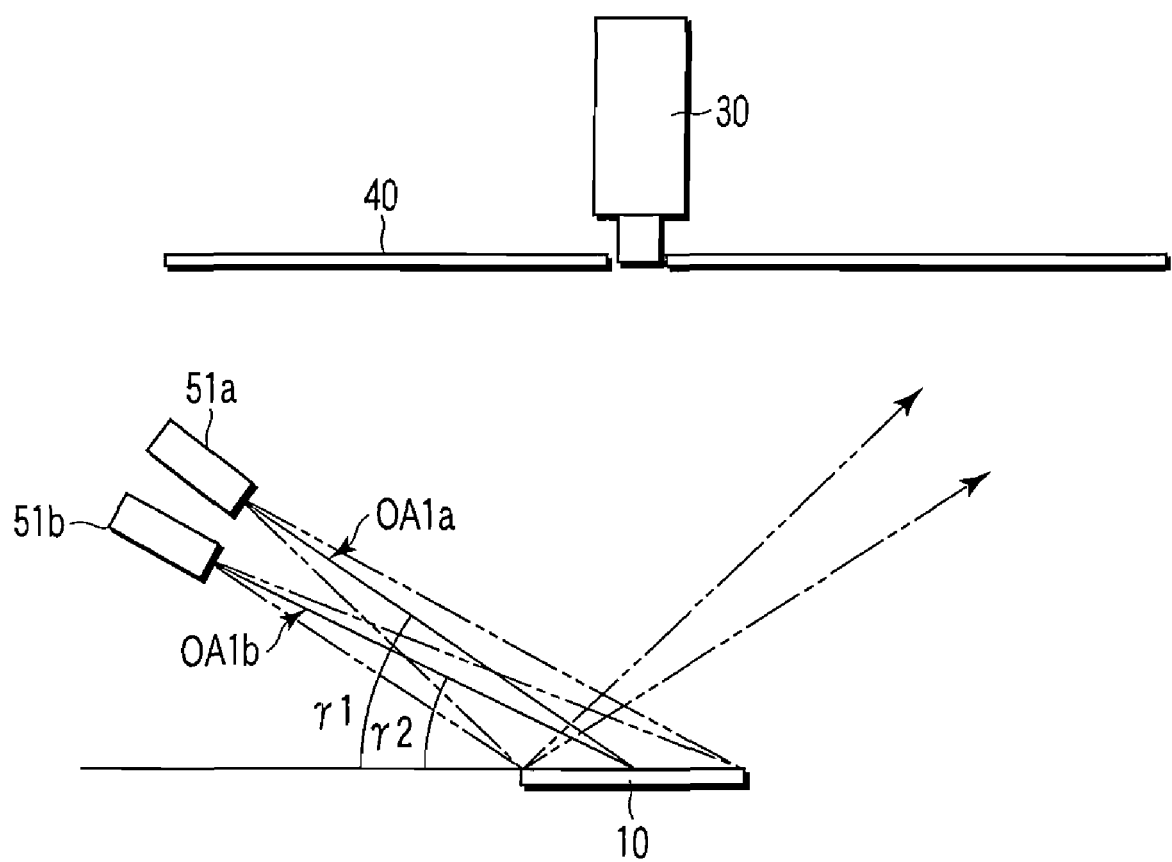
F I G. 3

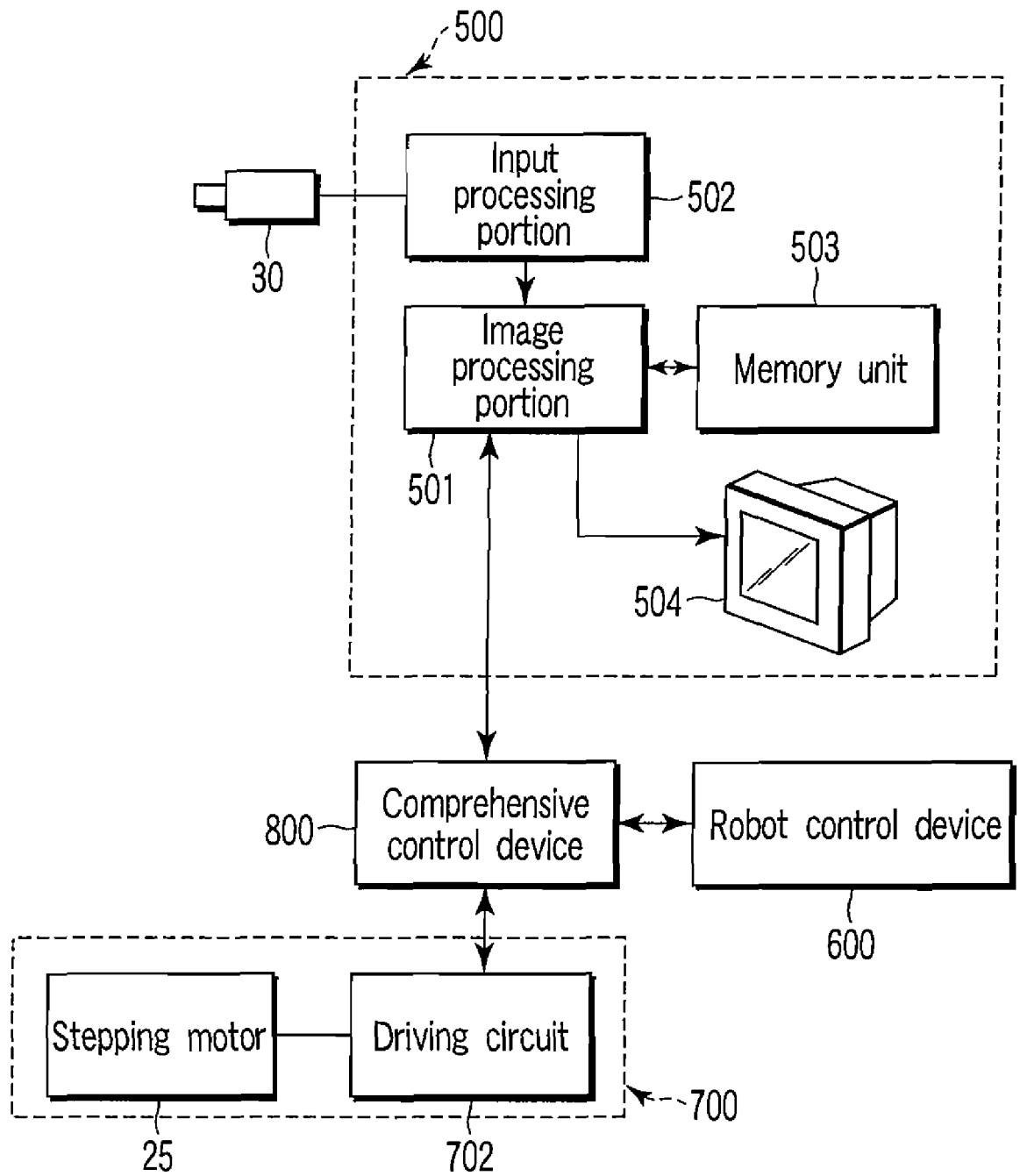
F I G. 4

SURFACE INSPECTION APPARATUS AND SURFACE INSPECTION METHOD FOR STRAINED SILICON WAFER

CROSS REFERENCE TO RELATED APPLICATIONS

This is a Continuation Application of PCT Application No. PCT/JP2006/306182, filed Mar. 27, 2006, which was published under PCT Article 21 (2) in Japanese.

This application is based upon and claims the benefit of priority from prior Japanese Patent Application No. 2005-093027, filed Mar. 28, 2005, the entire contents of which are incorporated herein by reference.

BACKGROUND OF THE INVENTION

1. Field of the Invention

The present invention relates to a surface inspection apparatus and a surface inspection method for a strained silicon wafer to inspect a surface strain caused by a dislocation (misfit dislocation) that occurs in a process of manufacturing the strained silicon wafer.

2. Description of the Related Art

In recent years, attention has been given to a strained silicon wafer to increase the operation speed of a silicon semiconductor device. For example, as shown in FIG. 11A, a strained silicon wafer 10 has a structure, in which a silicon substrate layer (Si substrate layer) 11 formed of monocrystalline silicon and a silicon germanium layer (SiGe layer) 12 having lattice spacing greater than that of the monocrystalline silicon and crystal-grown on the Si substrate layer 11, and a silicon layer (Si layer) 13 crystal-grown on the SiGe layer 12. The SiGe layer 12 is formed of a composition gradient SiGe region 12a, in which the germanium (Ge) concentration is gradually increased in the direction of thickness, and a relaxed SiGe region 12b, in which the germanium (Ge) concentration is substantially constant and which is formed on the composition gradient SiGe region 12a.

The strained silicon wafer 10 is not limited to the structure described above, but may have structures as shown in FIGS. 11B, 11C and 11D. In the example shown in FIG. 11B, an SiGe layer 12 of a uniform composition is formed on an Si substrate layer 11, and an Si layer 13 is crystal-grown on the SiGe layer 12. In the example shown in FIG. 11C, a silicon oxide layer 14 is formed on an Si substrate layer 11, a relaxed SiGe layer 12b is crystal-grown on the silicon oxide layer 14, and an Si layer 13 is crystal-grown on the relaxed SiGe layer 12b. This is called SGOI (Silicon Germanium on Insulator). In the example shown in FIG. 11D, a silicon oxide layer 14 is formed on an Si substrate 11, and an Si layer 13 is crystal-grown on the silicon oxide layer 14. This is called SSOI (Strained Silicon on Insulator).

In the strained silicon wafer 10 of the structure described above (refer to FIG. 11A), since the Si layer 13 is crystal-grown (epitaxial-grown) on the SiGe layer 12 (relaxed SiGe region 12b) having relatively great lattice spacing, strain occurs in the Si layer 13 (this Si layer is hereinafter referred to as the strained Si layer). Strain also occurs in the SiGe layer 12 because of lattice misfit between the Si substrate layer 11 and the SiGe layer 12 formed thereon. Because of these strains, specifically, dislocation (misfit dislocation) continuously occurs in the strained Si layer 13 in a direction along the lattice structure.

To judge whether the manufacturing process is appropriate or not, it is helpful to know a state of the strain caused by the dislocation in the strained Si layer 13 as a surface layer of the strained silicon wafer 10. The state of the strain caused by the dislocation in the strained Si layer 13 can be observed by X ray topography (XRT) (see, for example, "Analysis Handbook for ULSI Manufacturing" edited by Tsuneo Ajioka and Michihiko Inaba, pp. 392-397, Realize Inc., 1994). The X ray topography (XRT) is a method for observing a spatial distribution or size of crystal defects or lattice strain, utilizing diffraction of an X ray. More specifically, a diffraction ray only from a specific lattice surface is taken out. Then, a subtle contrast in the diffraction image, which occurs due to some defect resulting from, for example, dislocation in the diffraction image is observed in one-to-one correspondence with each part of the sample crystal. However, the inspection using the X ray topography (XRT) is basically destructive testing; that is, since the X ray need be irradiated on the strained silicon wafer 10 as a sample, the inspected strained silicon wafer cannot be utilized thereafter. In addition, since the X ray is used, it is troublesome to control the testing area.

When dislocation occurs in the process of growing a silicon layer on the SiGe layer 12 (relaxed SiGe region 12b), asperity strain resulting from the dislocation is generated on the surface of the strained Si layer 13, which is formed upon completion of the growth. Since the asperity strain on the surface is caused by the dislocation extending in the direction of the lattice structure of the strained Si layer 13, it may exhibit a lattice-shaped pattern (hereinafter referred to as cross-hatch pattern).

BRIEF SUMMARY OF THE INVENTION

When the surface of the strained silicon wafer 10 is visually inspected in a darkroom with irradiation of a light beam on the surface of the strained silicon wafer 10, only a part of the light diffracted by the cross-hatch pattern can be inspected as several bright lines. Even when the strained silicon wafer 10 is rotated, all of the cross-hatch pattern cannot be observed, although only some similar bright lines can be seen. Thus, the overall state of strain in the strained silicon wafer, resulting from the dislocation, cannot be grasped by the visual inspection.

The present invention has been made in consideration of those circumstances, and provides an inspection method and an inspection apparatus for a strained silicon wafer to grasp the overall state of strain caused by dislocation in the strained silicon layer of a strained silicon wafer without using an X ray.

Means for Solving the Problems

In a surface inspection method and an inspection apparatus for a strained silicon wafer according to the present invention, an image pickup device disposed in a predetermined position relative to a surface of a strained silicon wafer photographs the surface of the strained silicon wafer in a plurality of rotation angle positions on photographing conditions under which bright lines appearing on the surface of the strained silicon wafer can be photographed, in an environment where a light source device illuminates the surface of the strained silicon wafer which is rotating. A composite image in a predetermined angle position is generated from surface images of the strained silicon wafer in a plurality of rotation angle positions obtained by the image pickup device.

With the constitution described above, when the image pickup device photographs the surface of the rotating strained silicon wafer in the respective rotation angle positions, the surface images of the strained silicon corresponding to the respective rotation angle positions may include bright lines generated by diffraction lights in asperity strain caused by dislocation. When a composite image is generated from the surface images of the strained silicon corresponding to the respective rotation angle positions, bright lines extending in directions corresponding to the respective rotation angle positions are superimposed one on another in the composite image. Thus, since the bright lines extending in the directions corresponding to the respective rotation angle positions are superimposed one on another in the composite image, the composite image may include a plurality of bright lines arranged in a lattice.

To capture bright lines generated by diffraction lights from a larger part of the asperity strain, which is formed on the surface of a strained silicon wafer due to dislocation, it is preferable that the rotation angle positions where the surface of the strained silicon wafer is photographed be set as many as possible in one rotation.

Further, in the surface inspection method and the inspection apparatus for a strained silicon wafer according to the present invention, the generating a composite image includes: generating a differential image representing a difference between a surface image obtained by photographing in each of the rotation angle positions and a predetermined reference image; and generating a composite image by composing differential images in the respective rotation angle positions.

With the constitution described above, bright lines can be more emphasized in each of the differential images by appropriately setting the reference image. As a result, latticed bright lines can appear more clearly also in the composite image obtained by composing the differential images.

The photographing conditions are not particularly limited, as far as bright lines appearing on the surface of the strained silicon wafer can be photographed by the image pickup device. For example, the conditions may include an optical positional relationship among the image pickup device, the optical axis of the light source and the surface of the strained silicon wafer, illumination of the surface of the strained silicon wafer, or an exposure time of the image pickup device.

The surface inspection method and inspection apparatus for a strained silicon wafer according to the present invention may further comprise a feature of extracting brightness information indicative of brightness of bright lines that appear in the composite image from the composite image.

With the constitution described above, the degree of asperity strain generated by dislocation that occurs in the strained silicon wafer can be understood from brightness information indicative of the brightness of bright lines appearing in the composite image.

The brightness information is not particularly limited, as far as it can represent the brightness of bright lines appearing in the composite image. It may be either information indicative of an average brightness of bright lines appearing in a composite image or information indicative of a brightness distribution of the bright lines.

BRIEF DESCRIPTION OF THE SEVERAL VIEWS OF THE DRAWING

FIG. 2 is a diagram showing a positional relationship (1) between a direction of radiation of light from a light source unit and a strained silicon wafer;

FIG. 3 is a diagram showing a positional relationship (2) between a direction of radiation of light from a light source unit and a strained silicon wafer;

FIG. 4 is a block diagram showing a configuration of a control system of the inspection apparatus shown in FIG. 1;

DETAILED DESCRIPTION OF THE INVENTION

An embodiment of the present invention will be described below with reference to the accompanying drawings.

Figure 1A:
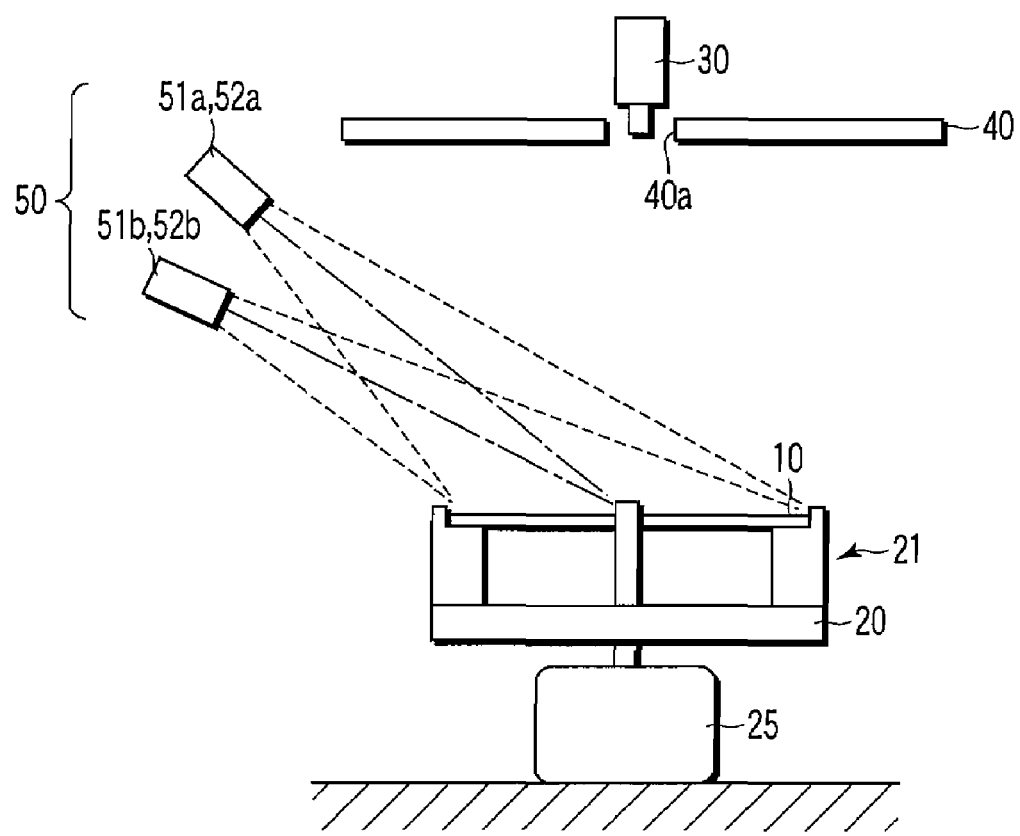
FIG. 1A is a side view showing a basic configuration of an inspection apparatus for use in a surface inspection method for a strained silicon wafer according to an embodiment of the present invention.
Figure 1B:
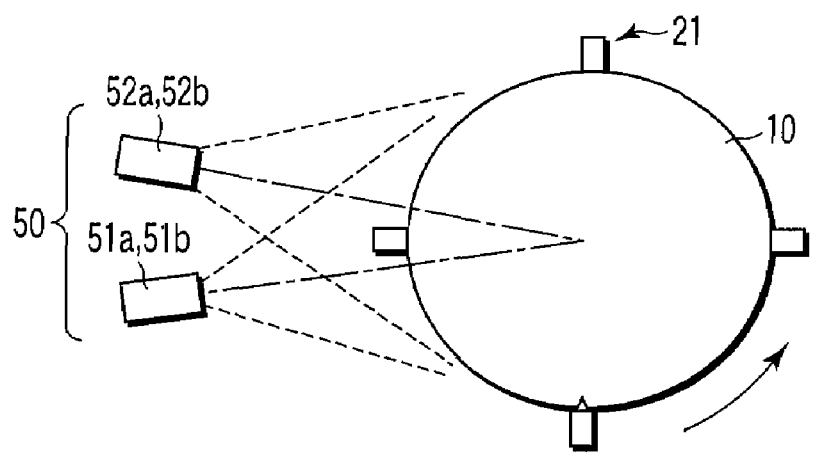
FIG. 1B is a plan view showing the basic configuration of the inspection apparatus shown in FIG. 1A.

An inspection apparatus for use in a surface inspection method for a strained silicon wafer according to an embodiment of the present invention has a configuration as shown in FIGS. 1A and 1B. FIG. 1A shows a basic configuration of an inspection apparatus, as viewed sideways, and FIG. 1B shows the basic configuration of the inspection apparatus as viewed from above.

In FIGS. 1A and 1B, the inspection apparatus includes a turntable 20, and a stepping motor 25 which is configured to repeatedly rotate the turntable 20 and stop it in a plurality of rotation angle positions. Wafer holding claw portions 21, which hold predetermined positions of the periphery of a strained silicon wafer 10 to be inspected, are provided on the turntable 20. The strained silicon wafer 10 is set on the wafer holding claw portions 21 with a strained silicon layer thereof directed upward.

A CCD camera (image pickup device) 30, a black shade 40 and a light source unit 50 are disposed above the turntable 20. The CCD camera 30 is arranged so as to image a surface of the strained silicon wafer 10 set on the wafer holding claw portions 21 on the turntable 20 through a hole 40a formed in the shade 40.

The CCD camera 30 maybe, for example, a monochrome area CCD camera (SKC141) of 1,300,000-pixel, 10-bit or 12-bit type produced by Ikegami Tsushin Co., Ltd. The lens mounted on the CCD camera 30 may be, for example, a 16 mm focal length, F/1.4 lens produced by TAMRON Co., Ltd.

The light source unit 50 is disposed so as to irradiate an inspection light on the turntable 20 at an inclined angle from above the strained silicon wafer 10. The inspection apparatus is arranged so as to keep a dark-field environment for the CCD camera 30.

The light source unit 50 includes light sources 51a, 51b, 52a and 52b. Each of the light sources 51a, 51b, 52a and 52b may be, for example, a metal halide lamp MME-G250 (250W) with an intense light guide and a converging lens (ML-50), produced by Moritex Corporation. Two light sources 51a and 52a arranged side by side are located in an upper portion and the other two light sources 51b and 52b also arranged side by side are located in a lower portion. In FIG. 1A, the light sources 51a and 52a arranged side by side are overlaid, and the other light sources 51b and 52b arranged side by side are overlaid. In FIG. 1B, the light sources 51a and 51b arranged one above the other are overlaid, and the other light sources 52a and 52b arranged one above the other are overlaid.

The four light sources 51a, 51b, 52a and 52b are arranged so that the optical axes thereof are not parallel with one another and cross one another at the center of rotation of the surface of the strained silicon wafer 10 set on the turntable 20. FIG. 2 shows a specific positional relationship between the light sources 51a and 52a arranged side by side in the upper portion. Specifically, the projection line of an optical axis OA1a of the light source 51a and the projection line of an optical axis OA2a of the light source 52a on a plane parallel to the surface of the strained silicon wafer 10 cross at an angle α. The angle α is set to, for example, 5°. The specific positional relationship between the light sources 51b and 52b arranged side by side in the lower portion is the same as that of the light sources 51a and 52a.

FIG. 3 shows a specific positional relationship between the light sources 51a and 51b arranged one above the other. Specifically, the optical axis OA1a of the light source 51a and the optical axis OA1b of the light source 51b are included in one plane perpendicular to the surface of the strained silicon wafer 10. In addition, an incident angle γ1 of an inspection light (optical axis OA1a) radiated from the light source 51a to the surface of the semiconductor wafer 10 is different from an incident angle γ2 of an inspection light (optical axis OA1b) radiated from the light source 51b to the surface of the semiconductor wafer 10. In general, an incident angle of a light beam to a plane is defined by an angle of the light beam with respect to the normal to the surface. However, in FIG. 3, since the optical axis OA1a of the light source 51a and the optical axis OA1b of the light source 51b are included in one plane perpendicular to the surface of the strained silicon wafer 10, the incident angles thereof are referred to as the angles of the optical axes with respect to the surface of the strained silicon wafer 10.

The positional relationship between the other light sources 52a and 52b arranged one above the other is the same as the positional relationship between the light sources 51a and 51b shown in FIG. 3. However, an incident angle of an inspection light radiated from the light source 52a with respect to the surface of the semiconductor wafer 10 is different from the incident angle (γ1) of the inspection light radiated from the light source 51a, and an incident angle of an inspection light radiated from the light source 52b with respect to the surface of the semiconductor wafer 10 is different from the incident angle (γ2) of the inspection light radiated from the light source 51b. Alternatively, the incident angle of the inspection light radiated from the light source 52a may be the same as the incident angle (γ1) of the inspection light radiated from the light source 51a, and the incident angle of the inspection light radiated from the light source 52b may be the same as the incident angle (γ2) of the inspection light radiated from the light source 51b.

FIG. 4 shows a processing system of the inspection apparatus described above.

Referring to FIG. 4, the processing system includes an inspection processing device 500, a robot control device 600 which drives and controls a sample carry-in robot mechanism (not shown) to carry and set the strained silicon wafer 10 on the wafer holding claw portions 21 of the turntable 20 and a sample carry-out robot mechanism (not shown) to carry out the strained silicon wafer 10 from the wafer holding claw portions 21 of the turntable 20, a turntable drive control device 700 which drives and controls the turntable 20 and a comprehensive control device 800. The comprehensive control device 800 performs comprehensive controls, such as timing control, of the inspection processing device 500, the robot control device 600 and the turntable drive control device 700.

The inspection processing device 500 has an image processing portion 501, an input processing portion 502, a memory unit 503 and a monitor unit 504. The input processing portion 502 performs processes, such as conversion of a photographing signal sent from the CCD camera 30, for example, serially in units of pixel, to parallel image data in units of pixel.

The input processing portion 502 has, for example, a PC-DIG produced by Coreco Inc. or its equivalent, as an image capture board which processes an image signal sent from the CCD camera 30.

The image processing portion 501 processes image data sent from the input processing portion 502 through steps described later, and generates a composite image composed of a plurality of surface images of the strained silicon wafer 10. The memory unit 503 stores various image data through processing of the image processing portion 501. The monitor unit 504 displays the composite image etc. obtained by the processing in the image processing portion 501.

The turntable drive control device 700 has a driving circuit 702 which drives the stepping motor 25. The driving circuit 702 rotates the stepping motor 25 in units of a predetermined angle based on a timing control signal from the comprehensive control device 800. Following the rotation of the stepping motor 25, the turntable 20 rotates.

Figure 11A:
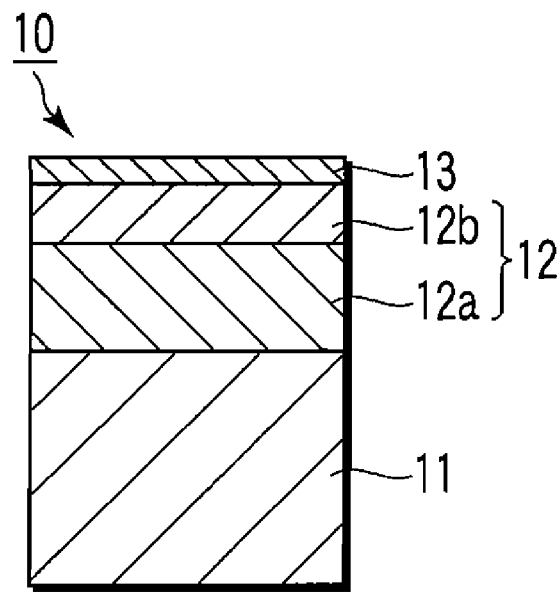
FIG. 11A is a diagram showing a first layered structure of a strained silicon wafer.
Figure 11B:
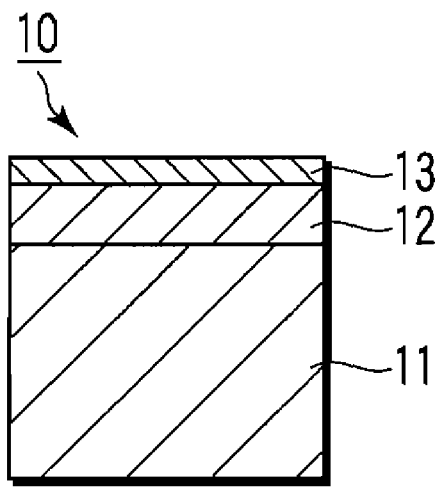
FIG. 11B is a diagram showing a second layered structure of a strained silicon wafer.
Figure 11C:
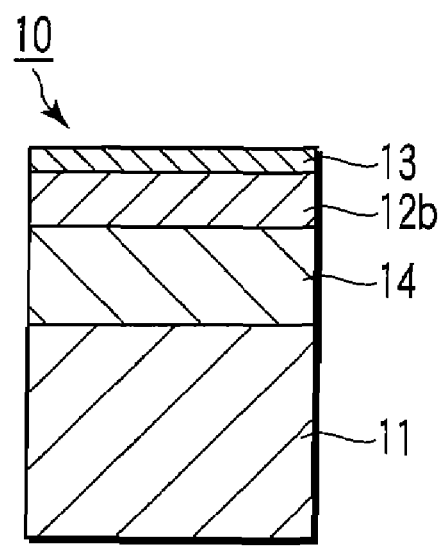
FIG. 11C is a diagram showing a third layered structure of a strained silicon wafer.
Figure 11D:
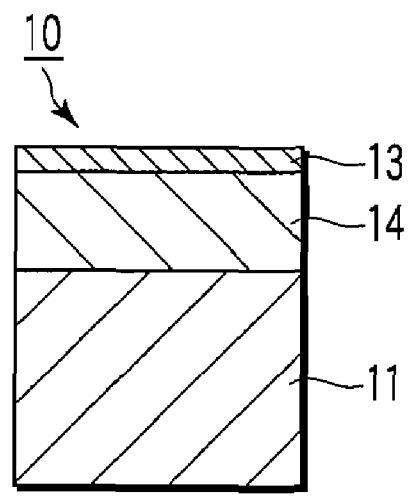
FIG. 11D is a diagram showing a fourth layered structure of a strained silicon wafer.

Inspection processing will now be described. In this embodiment, the strained silicon wafer 10 having the structure as shown in FIG. 11A is used.

In an environment where the surface of the strained silicon wafer 10 is radiated with the light from the light source unit 50, the CCD camera 30 takes an image of the surface of the strained silicon wafer 10 under photographing conditions which allow photographing of bright lines appearing on the strained silicon wafer 10 as will be described later.

At that time, the stepping motor 25 of the turntable drive control device 700 is rotated in units of a predetermined angle based on the timing control signal from the comprehensive control device 800 (see FIG. 4) of the control system. The driving of the stepping motor 25 causes the strained silicon wafer 10 to rotate in units of the predetermined angle. The CCD camera 30 photographs the surface of the strained silicon wafer 10 in rotation angle positions shifted at intervals of the predetermined angle. The inspection processing device 500 captures photographing signals from the CCD camera 30 under the control of the comprehensive control device 800.

In the inspection processing device 500, the input processing portion 502 converts a photographing signal from the CCD camera 30 to image data indicative of a brightness level in units of pixel, and supplies the image data to the image processing portion 501. The image processing portion 501 processes the image data supplied from the input processing portion 502 into image data for one frame indicative of an image of the surface of the strained silicon wafer 10, and stores the data as original image data in the memory unit 503. This processing is performed in synchronism with the rotation of the turntable 20, so that original image data indicative of the images of the surface of the silicon wafer 10 photographed N times by the CCD camera 30 in the respective angle positions are accumulated in the memory unit 503.

When the inspection lights from the four light sources 51a, 51b, 52a and 52b are irradiated on the surface of the strained silicon wafer 10 having asperity strain as a cross-hatch pattern resulting from the dislocation, four light beams travel in directions forced in angles with respect to the radiation directions (direction of the optical axes) of the four inspection lights. Thus, lights (diffraction lights) travel from the asperity strain in directions (directions of peaks of intensity distributions) depending on the respective directions of radiation of the four inspection lights. Therefore, the CCD camera 30 can capture the lights (bright lines) from the asperity strain at a higher possibility. When any of the lights that traveled from the asperity strain is incident in the CCD camera 30, the brightness level of the pixel corresponding to the bright line in the original image data, generated on the basis of the photographing signal sent from the CCD camera 30, becomes higher than the brightness level of any other pixel.

Figure 5:
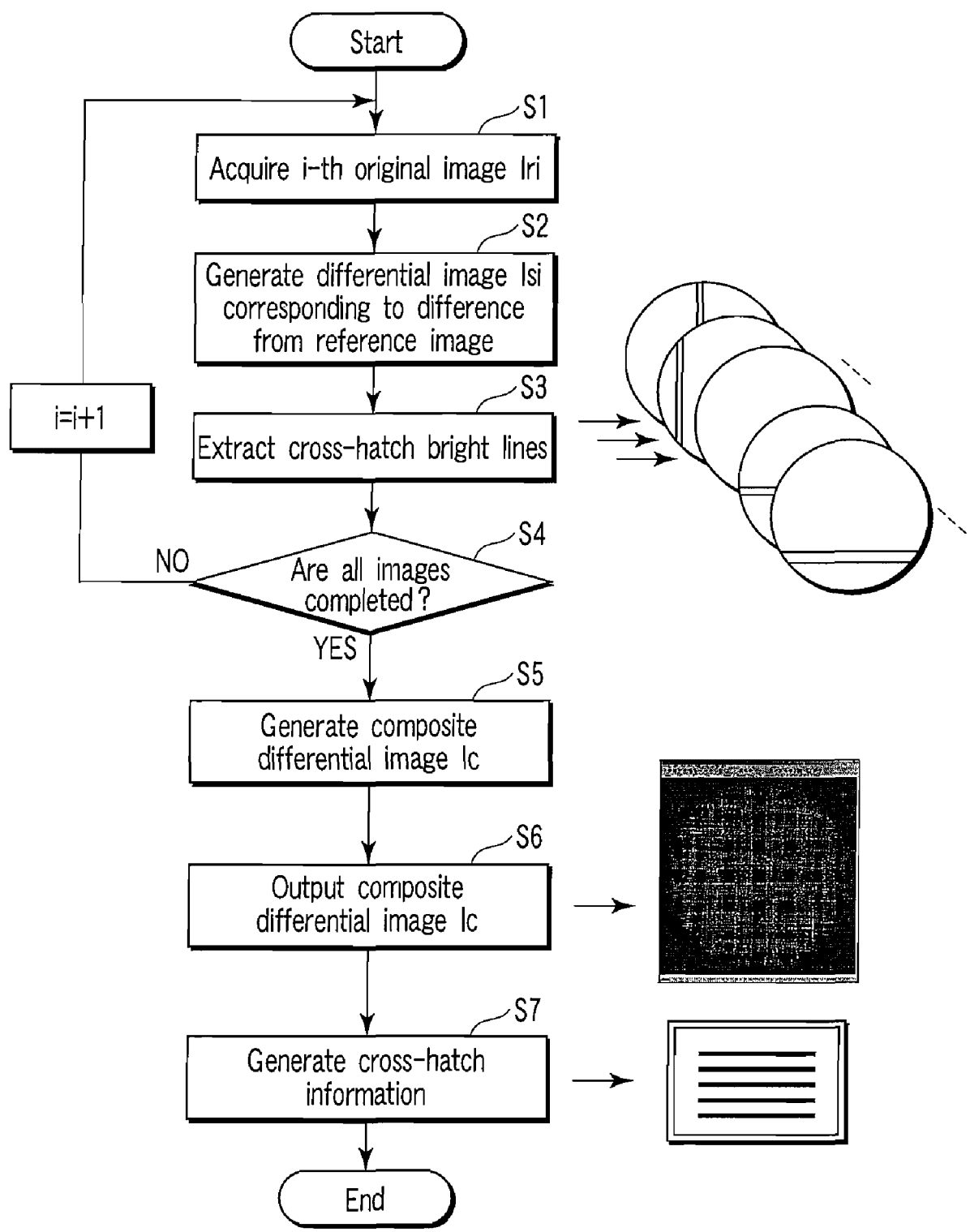
FIG. 5 is a flowchart showing processing sequences executed in an image processing portion of the control system shown in FIG. 1.

When the original image data corresponding to the N original images (surface images) is accumulated in the memory unit 503 as described above, the image processing portion 501 performs processing through the steps shown in FIG. 5.

Referring to FIG. 5, the image processing portion 501 acquires an i-th (initial value of i: 1) original image data Iri stored in the memory unit 503 (S1). The memory unit 503 stores reference image data (image data is hereinafter referred to simply as an image). The reference image may be a surface image of a wafer having no asperity strain of the aforementioned cross-hatch pattern (for example, a bear wafer). The image processing portion 501 generates a differential image Isi corresponding to a difference between the acquired original image Iri and the reference image. More specifically, the image processing portion 501 subtracts the brightness level of each pixel of the reference image from the brightness level of the corresponding pixel of the original image Iri. The differential image Isi is formed of the pixels of the brightness levels obtained as results of the subtractions. Therefore, it is assumed that a pixel of a relatively high brightness level in the differential image Isi corresponds to a bright line caused by the asperity strain which does not exist in the reference image. The differential image Isi thus generated is stored in the memory unit 503.

The image processing portion 501 performs threshold processing for the brightness levels of the respective pixels of the differential image Isi obtained as described above, thereby removing noises and extracting an area (a group of pixels) of the brightness levels assumed to correspond to the bright lines (S3). Then, the image processing portion 501 designates a next original image (i=i+1) and repeats the same processing (generation of the differential image Isi) as described above with respect to the next original image (S1, S2, S3 and S4), until it determines that the processing is completed for all of the original images (N original images) accumulated in the memory unit 503 (S4).

When the image processing portion 501 determines that the processing is completed for all of the original images accumulated in the memory unit 503 (YES in S4), it generates a composite differential image Ic by composing the N differential images accumulated in the memory unit 503. More specifically, the angles of the differential images are adjusted in accordance with the rotation angle positions at which the original images corresponding to the differential images are obtained. In other words, the differential images obtained in the respective rotation angle positions are converted to images in a predetermined rotation angle position. Then, brightness levels higher than a threshold value are extracted from the N brightness levels of the pixel in the same position of the angle-adjusted differential images. The highest level of the extracted brightness levels is determined as the brightness level of the pixel in that position. Through the above processing, necessary bright lines can be captured in a composite image without deterioration.

Upon generation of the composite differential image as described above, the image processing portion 501 displays the composite differential image Ic in the monitor unit 504 (S6).

The composite differential image Ic actually obtained by the processing of the inspection apparatus as described above will now be described.

As shown in FIGS. 1A, 1B, 2 and 3, the relative position of the light source unit 50, the CCD camera 30 and the surface of the silicon wafer 10 in the inspection apparatus was set as an optimal photographing condition to photograph bright lines that appear on the surface of the strained silicon wafer 10. In addition, the surface illumination of the strained silicon wafer 10 was set to, for example, 5000 lux, and the exposure time of the CCD camera 30 is set to, for example, 33 msec. as the photographing conditions.

Experiment 1

Figure 6:
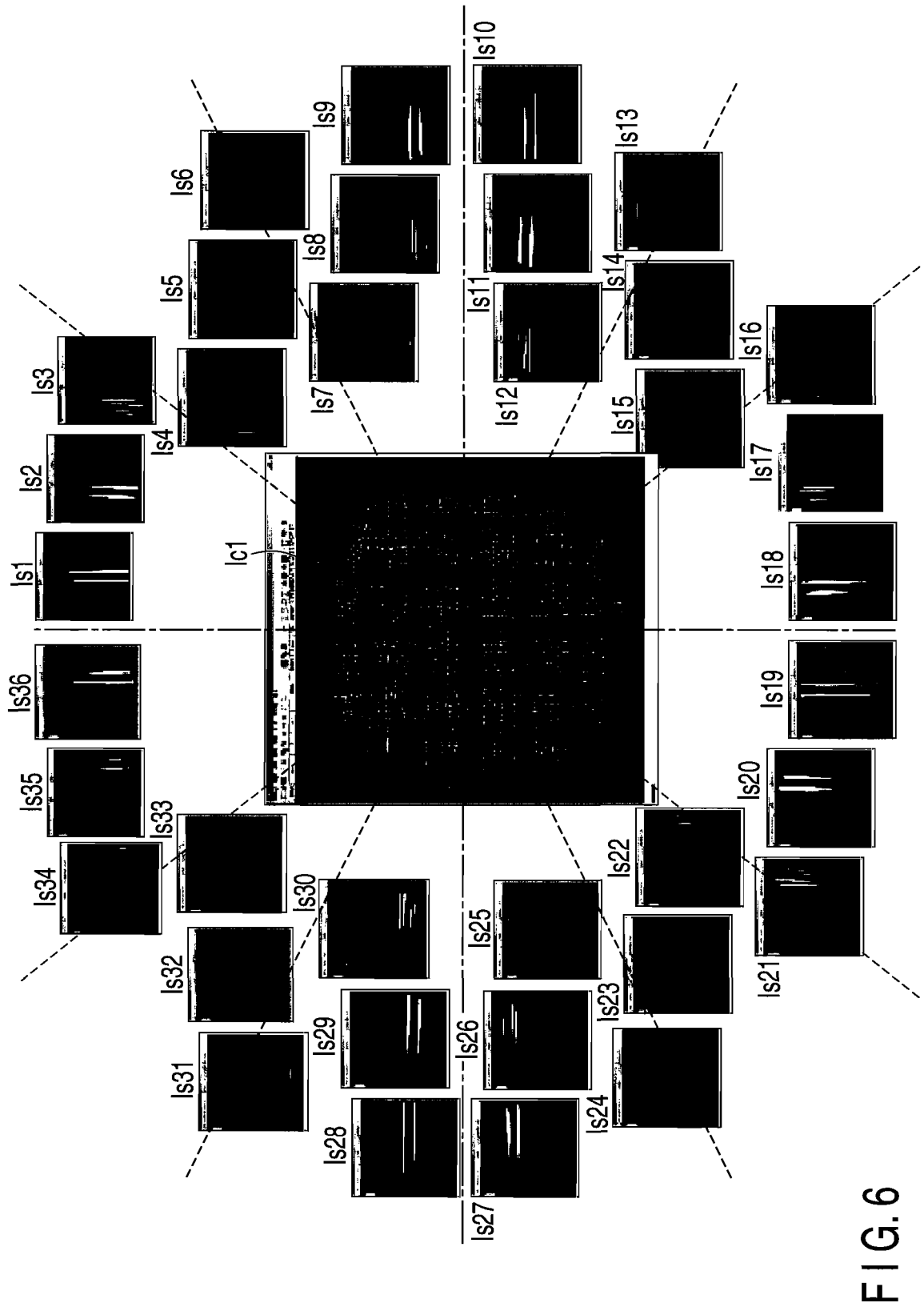
FIG. 6 is a diagram showing an example (1) of differential images and a composite differential image.

The surface of the strained silicon wafer 10 was photographed in rotation angle positions shifted at intervals of 10°. As a result, differential images Is1 to Is36 corresponding to 36 original images (surface images) as shown in FIG. 6 were obtained. The differential images Is1 to Is36 have been angle-adjusted so that the notch of the wafer is located at the lower end. In this experiment, bright lines extending in directions according to the photographed rotation angle positions appeared in the differential images Is1 to Is4, Is7 to Is13, Is17 to Is22, Is25 to Is31 and Is34 to Is36. A composite differential image Ic1, which was obtained by composing these differential images Is1 to Is36 so as to be superimposed one on another, included a number of bright lines latticed as shown in the central portion of FIG. 6.

Experiment 2

Figure 7:
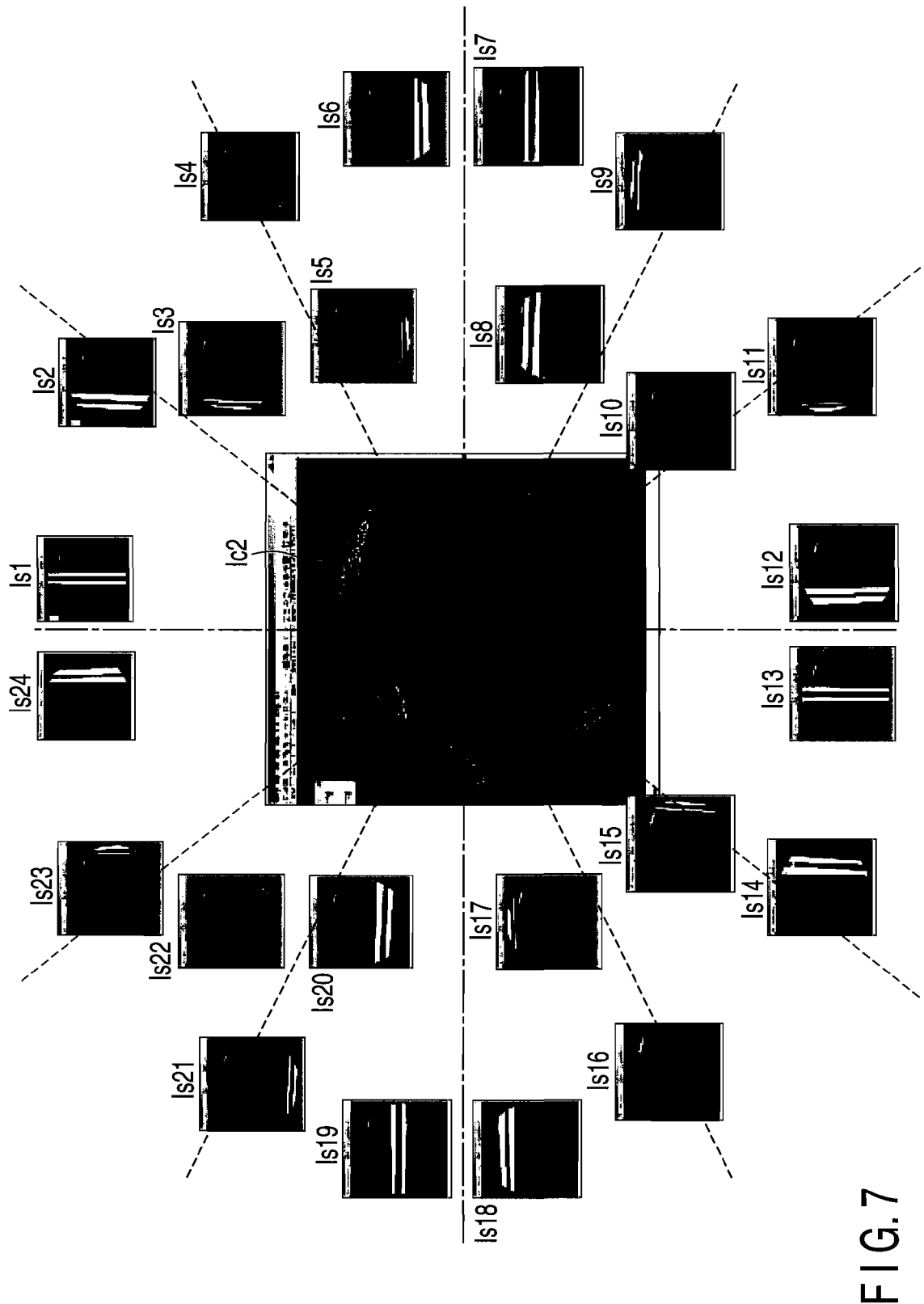
FIG. 7 is a diagram showing an example (2) of differential images and a composite differential image.

The surface of the strained silicon wafer 10 was photographed in rotation angle positions shifted at intervals of 15°. As a result, differential images Is1 to Is24 corresponding to 24 original images (surface images) as shown in FIG. 7 were obtained. The differential images Is1 to Is24 have also been angle-adjusted so that the notch of the wafer is located at the lower end. In this experiment, bright lines extending in directions according to the photographed rotation angle positions appeared in the differential images Is1 to Is3, Is5 to Is9, Is11 to Is15, Is18 to Is21, Is23 and Is24. A composite differential image Ic2, which was obtained by composing these differential images Is1 to Is24 so as to be superimposed one on another, included a plurality of bright lines latticed as shown in the central portion of FIG. 7. The number of bright lines that appeared in the composite differential image Ic2 shown in FIG. 7 is less than that in the composite differential image Ic1 shown in FIG. 6.

Experiment 3

Figure 8:
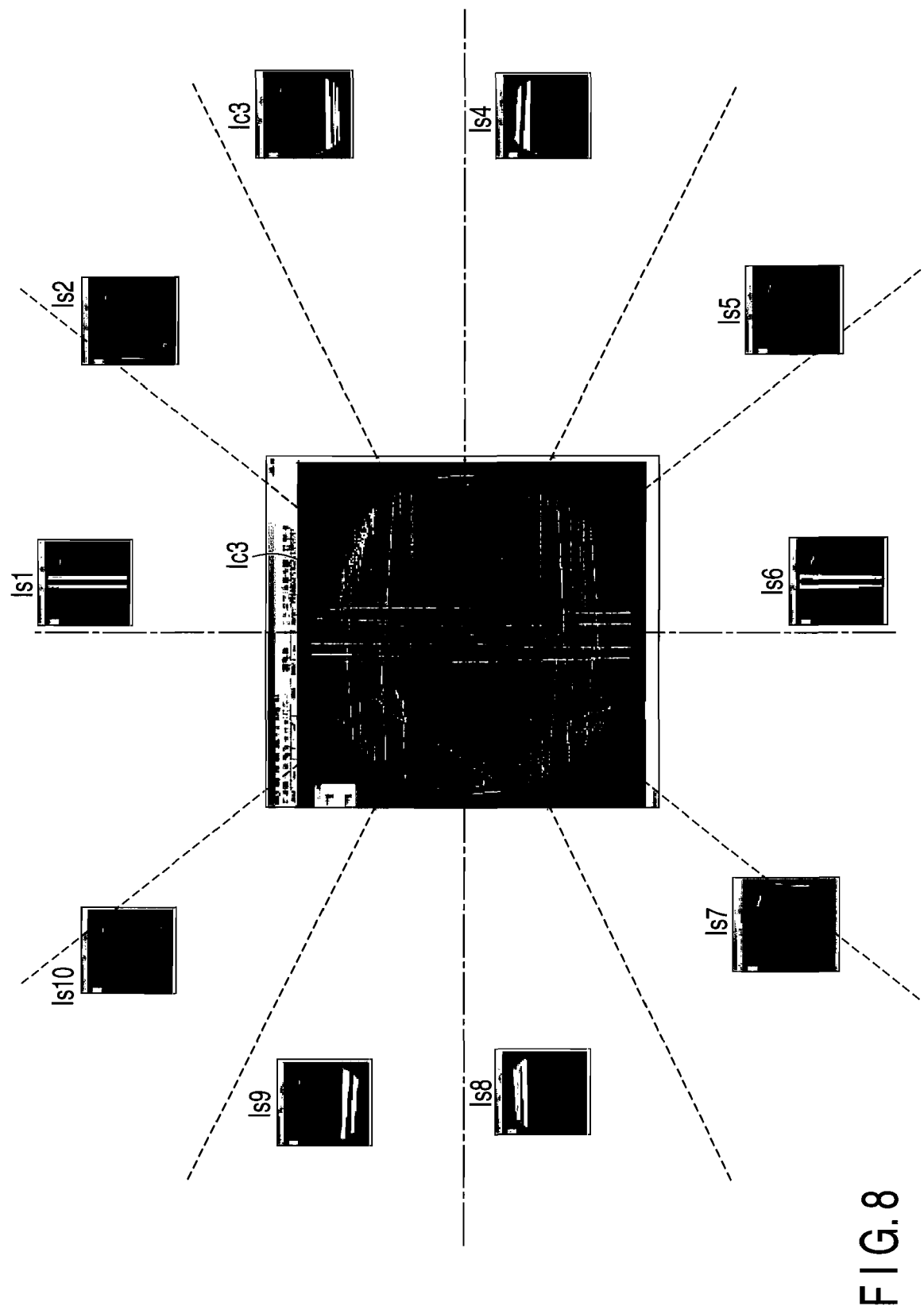
FIG. 8 is a diagram showing an example (3) of differential images and a composite differential image.

The surface of the strained silicon wafer 10 was photographed in rotation angle positions shifted at intervals of 36°. As a result, differential images Is1 to Is10 corresponding to 10 original images (surface images) as shown in FIG. 8 were obtained. The differential images Is1 to Is10 have also been angle-adjusted so that the notch of the wafer is located at the lower end as in the cases of Experiments 1 and 2. In this experiment, bright lines extending in directions according to the photographed rotation angle positions appeared in the differential images Is1, Is3, Is4, Is6, Is8 and Is9. A composite differential image Ic3, which was obtained by composing these differential images Is1 to Is10 so as to be superimposed one on another, included a plurality of bright lines latticed as shown in the central portion of FIG. 8. In the composite differential image Ic3 shown in FIG. 8, the bright lines are not so uniformly latticed as in the cases of the composite differential images Ic1 and Ic2 shown in FIGS. 6 and 7.

Figure 9A:
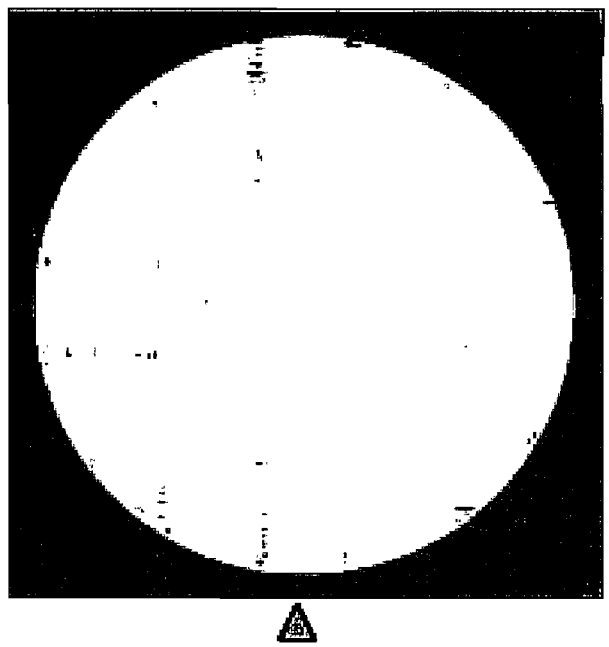
FIG. 9A is a diagram showing a lattice-shaped pattern of bright lines that appears in a composite differential image of a first example of various Ge concentrations.
Figure 9B:
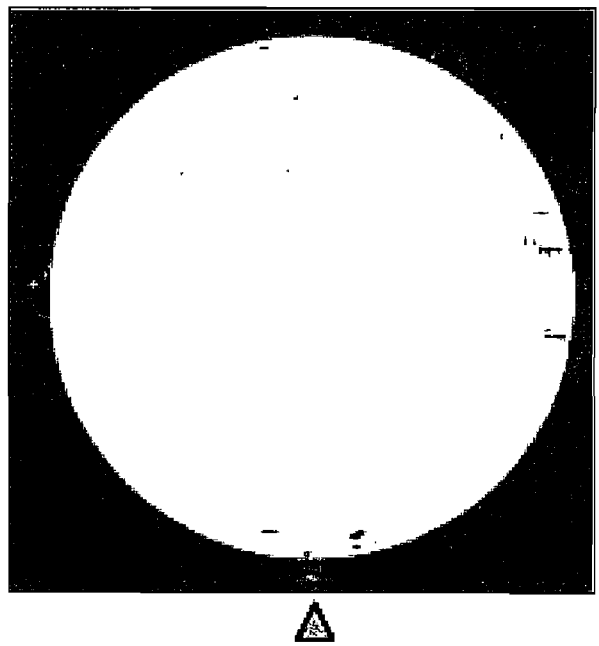
FIG. 9B is a diagram showing a lattice-shaped pattern of bright lines that appears in a composite differential image of a second example of various Ge concentrations.
Figure 9C:
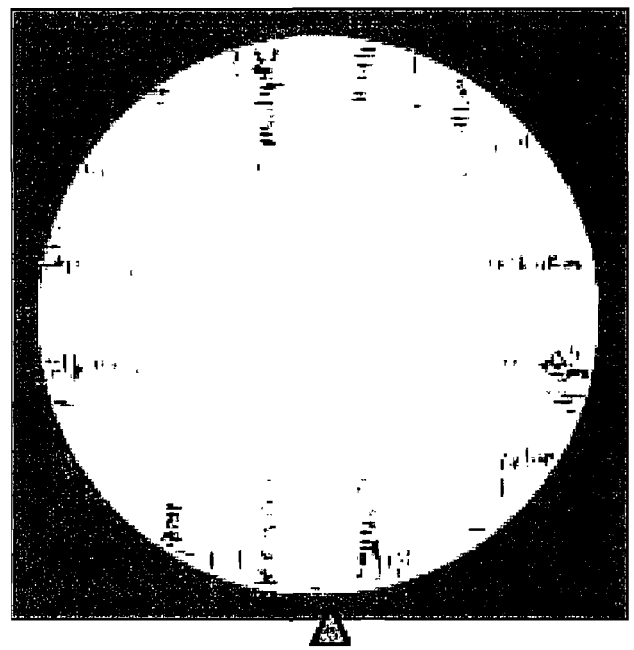
FIG. 9C is a diagram showing a lattice-shaped pattern of bright lines that appears in a composite differential image of a third example of various Ge concentration.
Figure 9D:
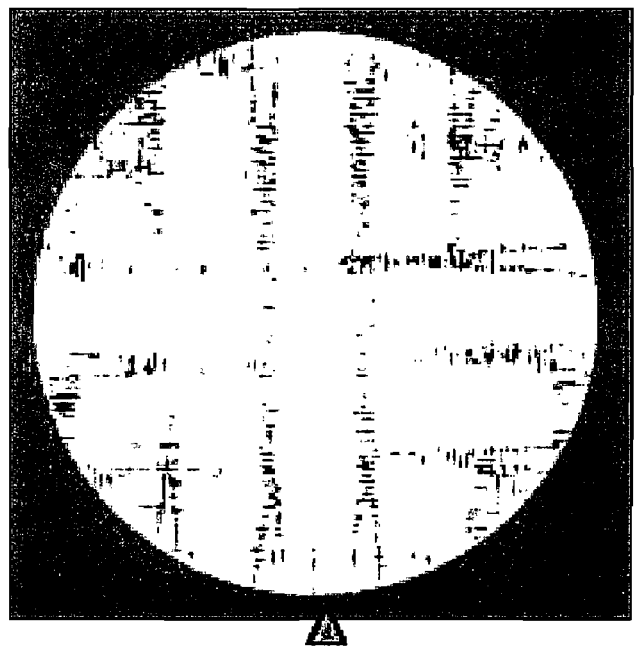
FIG. 9D is a diagram showing a lattice-shaped pattern of bright lines that appears in a composite differential image of a fourth example of various Ge concentrations.

A lattice-shaped pattern of bright lines that appear in a composite differential image (corresponding to the composite differential image Ic1 shown in FIG. 6), which is shown in FIG. 9D to be described later, was similar to a high-density distribution pattern of strain of the strained silicon layer 13 (see FIG. 11) of the same strained silicon wafer 10 observed by X ray topography. Thus, the lattice-shaped pattern of the bright lines that appear in the composite differential image Ic1 corresponds to the pattern of asperity strain formed on the surface of the strained silicon layer 13, caused by the dislocation that occurred in that layer. Therefore, the overall state of the strain caused by the dislocation that occurred in the strained silicon layer 13 can be grasped from the lattice-shaped pattern (cross hatch pattern) of bright lines appearing in the composite differential image Ic1 shown in FIG. 6.

To capture bright lines generated by diffraction lights from a larger part of the asperity strain, which is formed on the surface of a strained silicon wafer due to dislocation, it is preferable that the rotation angle positions where the surface of the strained silicon wafer is photographed be set as many as possible in one rotation. According to the experiments described above, it is preferable that the rotation angle positions for photographing be shifted at intervals of 10° or smaller. However, more memory capacity is required as the number of images (differential images) to be composed is increased. Therefore, the surface is actually photographed in as many rotation angle positions as possible (of the optimum number of positions) in consideration of the amount of information that can be stored within the memory capacity of the memory unit 503 shown in FIG. 4.

During photographing the surface of the strained silicon wafer 10 by the CCD camera 30 in rotation angle positions shifted at intervals of a predetermined angle, the strained silicon wafer 10 may be stopped at every predetermined angle position, or may be continuously rotated.

The applicants also inspected dependence of a lattice-shaped pattern of bright lines appearing in a composite differential image on a Ge concentration in the SiGe layer 12 (see FIG. 11) which lies under the strained Si layer 13. The photographing conditions are the same as those in the case of Experiments 1 to 3 described above. Composite differential images obtained through Experiments 4 to 7 described below are opposite in contrast from the images shown in FIGS. 6 to 8 (bright lines in FIGS. 6 to 8 correspond to dark lines in the following experiments).

Experiment 4

The strained silicon wafer 10 used in this experiment has the following structure.
Diameter: 8 inches
Strained Si layer 13: 12 nm
SiGe layer 12: Ge concentration 10% ($Si_{0.9}Ge_{0.1}$)
In this case, the lattice-shaped pattern of bright lines as shown in FIG. 9A appeared in the composite differential image.

Experiment 5

The strained silicon wafer 10 used in this experiment has the following structure.
Diameter: 8 inches
Strained Si layer 13: 12 nm
SiGe layer 12: Ge concentration 16% ($Si_{0.84}Ge_{0.16}$)
In this case, the lattice-shaped pattern of bright lines as shown in FIG. 9B appeared in the composite differential image.

Experiment 6

The strained silicon wafer 10 used in this experiment has the following structure.
Diameter: 8 inches
Strained Si layer 13: 0 nm
SiGe layer 12: Ge concentration 20% ($Si_{0.8}Ge_{0.2}$)
In this case, the lattice-shaped pattern of bright lines as shown in FIG. 9C appeared in the composite differential image.

Experiment 7

The strained silicon wafer 10 used in this experiment has the following structure.
Diameter: 8 inches
Strained Si layer 13: 16 nm
SiGe layer 12: Ge concentration 30% ($Si_{0.7}Ge_{0.3}$)
In this case, the lattice-shaped pattern of bright lines as shown in FIG. 9D appeared in the composite differential image.

From Experiments 4 to 7, it was recognized that the higher the Ge concentration of the SiGe layer 12 under the strained Si layer 13, the clearer the lattice-shaped pattern appearing in the composite differential image Ic. This would be because the higher the Ge concentration of the SiGe layer 12, the greater the degree of strain caused by dislocation in the strained Si layer 13. Therefore, it is considered that when a clear lattice-shaped pattern appears in the composite differential image Ic, the degree of the strain in the strained Si layer 13 is greater, and this is caused by the high Ge concentration in the underlying SiGe layer 12.

Further, the applicants inspected dependence of a lattice-shaped pattern of bright lines appearing in a composite differential image on a composition gradient of Ge in the SiGe layer 12 (see FIG. 11) which lies under the strained Si layer 13. The photographing conditions are the same as those in the case of Experiments 1 to 3 described above. As well as the images shown in FIGS. 9A to 9D, composite differential images obtained through Experiments 8 to 10 described below are also opposite in contrast from the images shown in FIGS. 6 to 8 (bright lines in FIGS. 6 to 8 correspond to dark lines in the following experiments).

Experiment 8

Figure 10A:
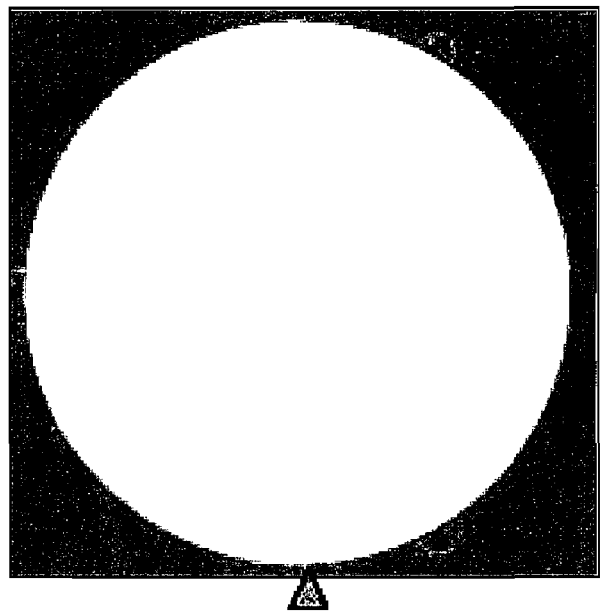
FIG. 10A is a diagram showing a lattice-shaped pattern of bright lines that appears in a composite differential image of a first example of various gradients of the Ge composition.

The strained silicon wafer 10 used in this experiment has the following structure.
Diameter: 8 inches
Strained Si layer 13: 12 nm
SiGe layer 12: Ge concentration 10% ($Si_{0.9}Ge_{0.1}$)
Ge composition gradient 2.5 Ge %
In this case, the lattice-shaped pattern of bright lines as shown in FIG. 10A appeared in the composite differential image. The lattice-shaped pattern of bright lines was almost unclear.

Experiment 9

Figure 10B:
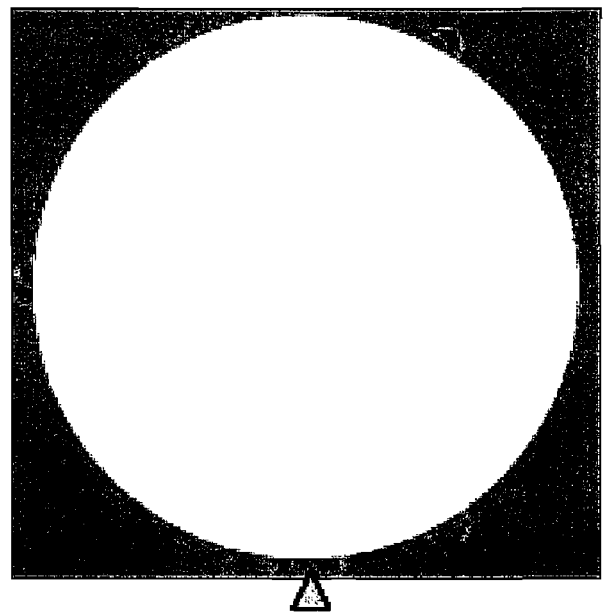
FIG. 10B is a diagram showing a lattice-shaped pattern of bright lines that appears in a composite differential image of a second example of various gradients of the Ge composition.

The strained silicon wafer 10 used in this experiment has the following structure.
Diameter: 8 inches
Strained Si layer 13: 12 nm
SiGe layer 12: Ge concentration 10% ($Si_{0.9}Ge_{0.1}$)
Ge composition gradient 5 Ge %
In this case, the lattice-shaped pattern of bright lines as shown in FIG. 10B appeared in the composite differential image. A very thin lattice-shaped pattern of bright lines appeared.

Experiment 10

Figure 10C:
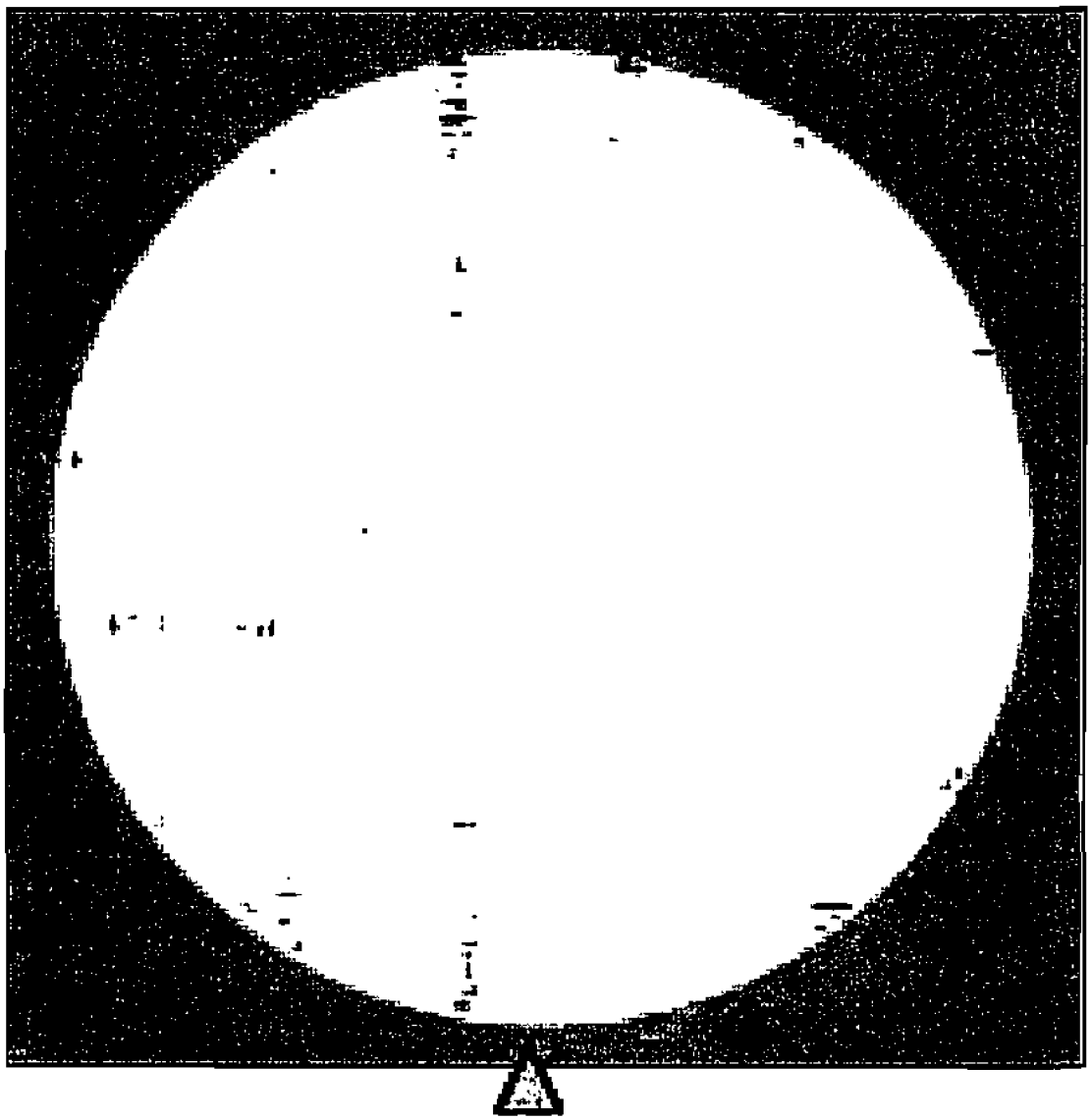
FIG. 10C is a diagram showing a lattice-shaped pattern of bright lines that appears in a composite differential image of a third example of various gradients of the Ge composition.

The strained silicon wafer 10 used in this experiment has the following structure.
Diameter: 8 inches
Strained Si layer 13: 12 nm
SiGe layer 12: Ge concentration 10% ($Si_{0.9}Ge_{0.1}$)
Ge composition gradient 10 Ge %
In this case, the lattice-shaped pattern of bright lines as shown in FIG. 10C appeared in the composite differential image. The lattice-shaped pattern of bright lines was brighter than those in the cases of Experiments 8 and 9.

From Experiments 8 to 10, it was recognized that the greater the Ge composition gradient of the SiGe layer 12 under the strained Si layer 13, the clearer the lattice-shaped pattern appearing in the composite differential image Ic. This would be because the greater the Ge composition gradient of the SiGe layer 12, the greater the degree of strain caused by dislocation in the strained Si layer 13. Therefore, it is considered that when a clear lattice-shaped pattern appears in the composite differential image Ic, the degree of the strain in the strained Si layer 13 is greater, and this is caused by the great Ge composition gradient of the underlying SiGe layer 12.

In the experiments described above, the surface illumination of the strained silicon wafer 10 was set to 5000 lux, and the exposure time of the CCD camera 30 was set to 33 msec. as the photographing conditions under which the CCD camera 30 can photograph the bright lines that appear on the surface of the silicon wafer 10. However, it was confirmed that the surface illumination might be 4000 lux to 6000 lux, and the exposure time might be 33 msec. to 67 msec.

Referring back to the processing flow shown in FIG. 5, after the composite differential image Ic as described above is displayed in the monitor unit 504, the image processing portion 501 generates cross-hatch information from the lattice-shaped pattern of bright lines that appear in the obtained composite differential image Ic (S7). The cross-hatch information may be, for example, a lattice interval, concentration, number, inclination, luminance, etc. of bright lines of the lattice-shaped pattern. The cross-hatch information can be displayed on the monitor unit 504 or printed out as text data.

As described above, the state (which may be qualitative information on the lattice-shaped pattern or the aforementioned cross-hatch information) of a lattice-shaped pattern appearing in the composite differential image Ic, through which the overall state of the strain caused by the dislocation in the strained silicon layer 13, is fed back to the conditions of a process of manufacturing the strained silicon wafer 10. As a result, a more appropriate strained silicon wafer 10 can be manufactured.

For example, after the bright lines of the lattice-shaped pattern appearing in the composite differential image Ic, as shown in FIGS. 6-8 and 9A to 9D, are subjected to a predetermined threshold process, if an average brightness or a brightness distribution of the remaining bright lines is to be included in the cross-hatch information, it is possible to adjust the concentration of Ge to be added for crystal growth of the SiGe layer 12 in the process of manufacturing a strained silicon wafer based on the average brightness or the brightness distribution (see Experiments 4 to 7). It is also possible to adjust the composition gradient of Ge to be added for crystal growth of the SiGe layer 12 in the manufacturing process (see Experiments 8 to 10).

According to a surface inspection apparatus and a surface inspection method for a strained silicon wafer of the present invention, a composite image in the predetermined rotation angle position is generated from surface images respectively photographed in a plurality of rotation angle positions of a strained silicon wafer, and the composite image thus generated can include bright lines of a lattice-shaped pattern. Therefore, the composite pattern can represent a cross-hatch pattern of asperity strain formed on the surface of the strained silicon wafer caused by a dislocation. Consequently, the overall state of the strain caused by the dislocation of the strained silicon layer in the strained silicon wafer can be grasped from the state of the composite image obtained without using an X ray.

What is claimed is:

1. A surface inspection method for inspecting strain that occurs in a surface layer of a strained silicon wafer, the method comprising:
    illuminating a surface of the strained silicon wafer;
    photographing, in a plurality of rotation angle positions, bright lines that appear on the surface of the strained silicon wafer, which is rotated in an environment where the surface of the strained silicon wafer is illuminated;
    generating a composite image from surface images of the strained silicon wafer photographed in the plurality of rotation angle positions; and
    determining the strain in the surface layer of the strained silicon wafer based on information obtained from the bright lines in the composite image.

2. The surface inspection method according to claim 1, wherein the generating a composite image includes: generating a differential image representing a difference in brightness between a surface image obtained by photographing in each of the rotation angle positions and a predetermined reference image; and generating a composite image by composing differential images in the respective rotation angle positions.

3. The surface inspection method according to claim 1, wherein the photographing is carried out under photographing conditions including at least brightness of the surface of the strained silicon wafer and an exposure time in the photographing.

4. The surface inspection method according to claim 1, further comprising extracting brightness information indicative of brightness of bright lines that appear in the composite image from the composite image.

5. A surface inspection apparatus for inspecting strain that occurs on a surface of a strained silicon wafer, the apparatus comprising:

illuminating means for illuminating the surface of the strained silicon wafer;

drive control means for rotating the strained silicon wafer in a circumferential direction;

photographing means for photographing, in a plurality of rotation angle positions, bright lines that appear on the surface of the strained silicon wafer in an environment where the surface of the strained silicon wafer is illuminated;

image processing means for generating a composite image from surface images of the strained silicon wafer photographed in the plurality of rotation angle positions;

output means for outputting information on the bright lines to inspect the strain in a silicon layer of the composite image generated by the image processing means; and determining the strain in the surface layer of the strained silicon wafer based on information obtained from the bright lines in the composite image.

6. The surface inspection apparatus according to claim 5, wherein the illuminating means illuminate the surface of the strained silicon wafer, while keeping a dark-field environment for the photographing means.

7. The surface inspection apparatus according to claim 5, wherein the illuminating means include a plurality of light sources, optical axes of which are not parallel to each other and cross at a center of rotation of the strained silicon wafer.

8. The surface inspection apparatus according to claim 5, wherein the drive control means comprise a turntable on which the strained silicon wafer is held, and a stepping motor which drives and rotates the turntable by a predetermined angle.

\* \* \* \* \*